United States Patent
Jacobs et al.

(10) Patent No.: US 10,535,425 B2
(45) Date of Patent: Jan. 14, 2020

(54) INVENTORY MANAGEMENT

(71) Applicant: PerceptiMed, Inc., Mountain View, CA (US)

(72) Inventors: Alan Jeffrey Jacobs, Palo Alto, CA (US); Ram Subramanian, Newark, CA (US)

(73) Assignee: PerceptiMed, Inc., Mountain View, CA (US)

( * ) Notice: Subject to any disclaimer, the term of this patent is extended or adjusted under 35 U.S.C. 154(b) by 12 days.

(21) Appl. No.: 16/022,475

(22) Filed: Jun. 28, 2018

(65) Prior Publication Data
US 2019/0006036 A1   Jan. 3, 2019

Related U.S. Application Data

(60) Provisional application No. 62/526,327, filed on Jun. 28, 2017.

(51) Int. Cl.
*G06Q 10/08* (2012.01)
*G16H 20/13* (2018.01)
(Continued)

(52) U.S. Cl.
CPC .......... *G16H 20/13* (2018.01); *G06Q 10/087* (2013.01); *G06Q 10/0833* (2013.01); *G09F 3/02* (2013.01);
(Continued)

(58) Field of Classification Search
None
See application file for complete search history.

(56) References Cited

U.S. PATENT DOCUMENTS

| 6,088,856 | A | 7/2000 | Boyer |
| 6,972,682 | B2 | 12/2005 | Lareau et al. |

(Continued)

FOREIGN PATENT DOCUMENTS

| CN | 1701327 A | 11/2005 |
| CN | 101568909 A | 10/2009 |

(Continued)

OTHER PUBLICATIONS

Lebhar-Friedman Inc, Hi-School to pioneer test of will-call prescription-tracking system, Aug. 18, 2003, Drug Store News, vol. 25 Iss. 10, p. 76 (Year: 2003).*

(Continued)

*Primary Examiner* — Dennis W Ruhl
*Assistant Examiner* — William G Lultschik
(74) *Attorney, Agent, or Firm* — Fenwick & West LLP

(57) ABSTRACT

A prescription management system receives prescription information and manages containers filled with the prescription. The prescription is stored in the container and the container is attached to a tracking device storing prescription information. The tracking device is managed by the prescription management system. The tracking device activates an indicator when it receives a request from the prescription management system identifying the tracking device. The indicator permits a user, such as a pharmacist, to locate a desired prescription. In some instances, filled prescriptions may be stored in a filled prescription holding area for a long period of time (i.e., the customer hasn't picked up the prescription). The system allows a user to identify these filled prescriptions and return the medication back to available stock for filling future prescriptions. The system may also identify these filled prescriptions and have the filled prescriptions delivered to a customer's home before the prescriptions expire.

11 Claims, 9 Drawing Sheets

(51) Int. Cl.
  *G09F 3/02*   (2006.01)
  *G16H 20/10*  (2018.01)
(52) U.S. Cl.
  CPC ..... *G16H 20/10* (2018.01); *G09F 2003/0216* (2013.01); *G09F 2003/0273* (2013.01)

(56) References Cited

U.S. PATENT DOCUMENTS

| | | | |
|---|---|---|---|
| 7,053,753 | B2 | 5/2006 | Kacalek et al. |
| 7,496,521 | B1 | 2/2009 | Louie et al. |
| 8,113,438 | B1 | 2/2012 | Leason et al. |
| 8,306,651 | B2 | 11/2012 | Chudy et al. |
| 2002/0104848 | A1 | 8/2002 | Burrows et al. |
| 2002/0169635 | A1 | 11/2002 | Shillingburg |
| 2004/0064215 | A1 | 4/2004 | Greeven et al. |
| 2004/0124988 | A1 | 7/2004 | Leonard et al. |
| 2005/0098626 | A1* | 5/2005 | Jordan ............... B65G 1/045 235/381 |
| 2005/0253703 | A1 | 11/2005 | He et al. |
| 2006/0265102 | A1* | 11/2006 | Bain ............... G06F 19/3462 700/237 |
| 2007/0023512 | A1 | 2/2007 | Miller et al. |
| 2007/0188306 | A1 | 8/2007 | Tethrake et al. |
| 2007/0204497 | A1 | 9/2007 | de la Huerga |
| 2008/0035520 | A1 | 2/2008 | Caracciolo et al. |
| 2008/0218358 | A1 | 9/2008 | Derrick et al. |
| 2009/0037575 | A1 | 2/2009 | Crystal et al. |
| 2009/0230189 | A1 | 9/2009 | Louie et al. |
| 2009/0230778 | A1 | 9/2009 | Alfven et al. |
| 2009/0322510 | A1 | 12/2009 | Berger et al. |
| 2010/0007464 | A1 | 1/2010 | McTigue |
| 2010/0030371 | A1 | 2/2010 | Chudy et al. |
| 2010/0049635 | A1 | 2/2010 | Delaney et al. |
| 2010/0238039 | A1 | 9/2010 | Tethrake et al. |
| 2011/0054668 | A1 | 3/2011 | Holmes et al. |
| 2011/0060457 | A1 | 3/2011 | De Vrught et al. |
| 2011/0068906 | A1 | 3/2011 | Shafer et al. |
| 2011/0131096 | A1 | 6/2011 | Frew et al. |
| 2011/0279245 | A1 | 11/2011 | Hynes et al. |
| 2012/0056000 | A1 | 3/2012 | Shores |
| 2013/0253700 | A1 | 9/2013 | Carson et al. |
| 2013/0297325 | A1 | 11/2013 | Cobb et al. |
| 2015/0169843 | A1 | 6/2015 | Jacobs et al. |
| 2015/0170097 | A1 | 6/2015 | Jacobs et al. |
| 2016/0110518 | A1 | 4/2016 | Louie et al. |
| 2017/0053099 | A1* | 2/2017 | Coughlin ............ G06F 19/3462 |
| 2017/0076063 | A1* | 3/2017 | Louie ............... G06F 19/3456 |
| 2018/0032680 | A1* | 2/2018 | Chen ............... G16H 10/60 |

FOREIGN PATENT DOCUMENTS

| | | | |
|---|---|---|---|
| CN | 101918949 | A | 12/2010 |
| CN | 102473255 | A | 5/2012 |
| JP | S 61-155106 | A | 7/1986 |
| JP | H05-128376 | A | 5/1993 |
| JP | H06-271023 | A | 9/1994 |
| JP | H07-247009 | A | 9/1995 |
| JP | 3024113 | U | 5/1996 |
| JP | 2000204810 | A | 7/2000 |
| JP | 2002-019928 | A | 1/2002 |
| JP | 2002-092165 | A | 3/2002 |
| JP | 2003-507819 | A | 2/2003 |
| JP | 2004-065986 | A | 3/2004 |
| JP | 2004-148120 | A | 5/2004 |
| JP | 2006-004119 | A | 1/2006 |
| JP | 2006-209287 | A | 8/2006 |
| JP | 2010-500128 | A | 1/2010 |
| JP | 2010-023952 | A | 2/2010 |
| JP | 2013-529095 | A | 7/2013 |
| WO | WO 01/15006 | A1 | 3/2001 |
| WO | WO 2011/112606 | A1 | 9/2011 |
| WO | WO 2013/112591 | A1 | 8/2013 |

OTHER PUBLICATIONS

Lebhar-Friedman Inc, Hi-School to pioneer test of will-call prescription-tracking system, Aug. 18, 2003, Drug Store News, vol. 25 Iss. 10, p. 76 (Year: 2003) (Year: 2003).*
Australian First Examination Report, Australian Application No. 2013305512, dated Jan. 15, 2018, 3 pages.
Australian Second Examination Report, Australian Application No. 2013305512, dated Aug. 13, 2018, 3 pages.
Australian First Examination Report, Australian Application No. 2013305511, dated Jan. 22, 2018, 3 pages.
Australian Second Examination Report, Australian Application No. 2013305511, dated Jul. 12, 2018, 3 pages.
Canadian First Office Action, Canadian Application No. 2,882,273, dated May 12, 2016, 3 pages.
Canadian Second Office Action, Canadian Application No. 2,882,273, dated Apr. 4, 2017, 6 pages.
Canadian Third Office Action, Canadian Application No. 2,882,273, dated Apr. 4, 2018, 4 pages.
Canadian First Office Action, Canadian Application No. 2,882,271, dated May 30, 2016, 4 pages.
Canadian Second Office Action, Canadian Application No. 2,882,271, dated May 15, 2017, 4 pages.
Canadian Third Office Action, Canadian Application No. 2,882,271, dated May 3, 2018, 4 pages.
Chinese First Office Action, Chinese Application No. 201380055767.8, dated Jun. 1, 2017, 27 pages.
Chinese Second Office Action, Chinese Application No. 201380055767.8, dated Nov. 24, 2017, 31 pages.
Chinese Third Office Action, Chinese Application No. 201380055767.8, dated Aug. 20, 2018, 28 pages.
Chinese First Office Action, Chinese Application No. 201380055791.1, dated Oct. 8, 2016, 22 pages.
Chinese Second Office Action, Chinese Application No. 201380055791.1, dated May 31, 2017, 20 pages.
Chinese Third Office Action, Chinese Application No. 201380055791.1, dated Nov. 30, 2017, 16 pages.
Chinese Fourth Office Action, Chinese Application No. 201380055791.1, dated Jun. 4, 2018, 17 pages.
Japanese First Office Action, Japanese Application No. 2015-528716, dated Jul. 25, 2017, 6 pages.
Japanese First Office Action, Japanese Application No. 2015-528715, dated Sep. 19, 2017, 6 pages.
Japanese Second Office Action, Japanese Application No. 2015-528715, dated May 29, 2018, 11 pages.
PCT International Search Report and Written Opinion, PCT Application No. PCT/US13/56690, dated Dec. 16, 2013, 13 pages.
PCT Invitation to Pay Additional Fees, PCT Application No. PCT/US13/56691, dated Dec. 5, 2013, 2 pages.
PCT International Search Report and Written Opinion, PCT Application No. PCT/US13/56691, dated Jan. 31, 2014, 24 pages.
PCT International Search Report and Written Opinion, PCT Application No. PCT/US18/40131, dated Sep. 6, 2018, 15 pages.
PCT International Search Report and Written Opinion, PCT Application No. PCT/US2018/040136, dated Sep. 14, 2018, 13 pages.

* cited by examiner

INVENTORY MANAGEMENT

CROSS REFERENCE TO RELATED APPLICATION

This application claims benefit of U.S. Provisional Application No. 62/526,327, filed Jun. 28, 2017, which is incorporated by reference in its entirety.

BACKGROUND

This invention relates generally to management systems and in particular to management systems of a pharmaceutical working environment.

Pharmacies fill and deliver to customers more than 4 billion prescriptions each year in the United States. The average retail store fills 200-400 customer prescriptions each day. Customers do not necessarily pick up these prescriptions the same day they are filled. Filled prescriptions are typically held for 1-2 weeks or more before returned to stock if not picked up. The will call process and storage bins in retail pharmacies must organize and hold hundreds to thousands of filled prescriptions awaiting pickup. One of the challenges in managing this large volume of filled prescriptions includes the time a cashier spends searching the will call bins for a waiting customer's prescription. This translates into the time customers spend in line waiting to pick their prescriptions and affects customer satisfaction. Errors in filing prescriptions in the wrong bin can lead to misplaced prescriptions that must be refilled while the customer waits, or prolonged time spent searching the store for the prescription.

When customers do not pick up their prescriptions, pharmacies need to retrieve these aged prescriptions from the will call bins to return the unused medications to stock. Locating and retrieving these aged prescriptions from among the hundreds to thousands of packages in the will call bins is a time-consuming process for pharmacy staff.

More efficient and cost effect solutions are needed for the storage and retrieval of filled prescriptions in the retail pharmacy environment.

SUMMARY

A prescription management system receives prescription information and manages containers filled with the prescription. The prescription management system receives an indication from a pharmacist or a prescription filling system that a particular container is filled with a prescription. The container is stored in a pharmacy, and an indicator on the container is activated when the prescription in the desired container is required. The indicator can be an audio or visual indicator that the pharmacist can use to identify the container. In some instances, the system may detect an event associated with the stored prescription that prevents the prescription from being dispensed to a customer. For example, the storage container may be tampered with, the prescription may require additional verification, or a consultation must be given to the customer first. Once the appropriate remedial action has taken place, the system allows the prescription to be dispensed to the customer. In some instances, filled prescriptions may be stored in a filled prescription holding area for a long period of time (i.e., the customer hasn't picked up the prescription). The system allows a user to identify these filled prescriptions and return the medication back to available stock for filling future prescriptions. The system may also identify these filled prescriptions and have the filled prescriptions delivered to a customer's home before the prescriptions expire.

While the prescription management system is described as managing prescription containers, the system can be used for organizations of medications outside of the pharmacy environment, such as within hospitals or nursing homes, or for organization of other items besides medications. For example, the system can be used for organizing and tracking different types of products within a store, for tracking books in a library, for tracking files in an office, for home use to track audio or video content or any other situation in which organizing, tracking and being able to quickly locate various items is beneficial.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
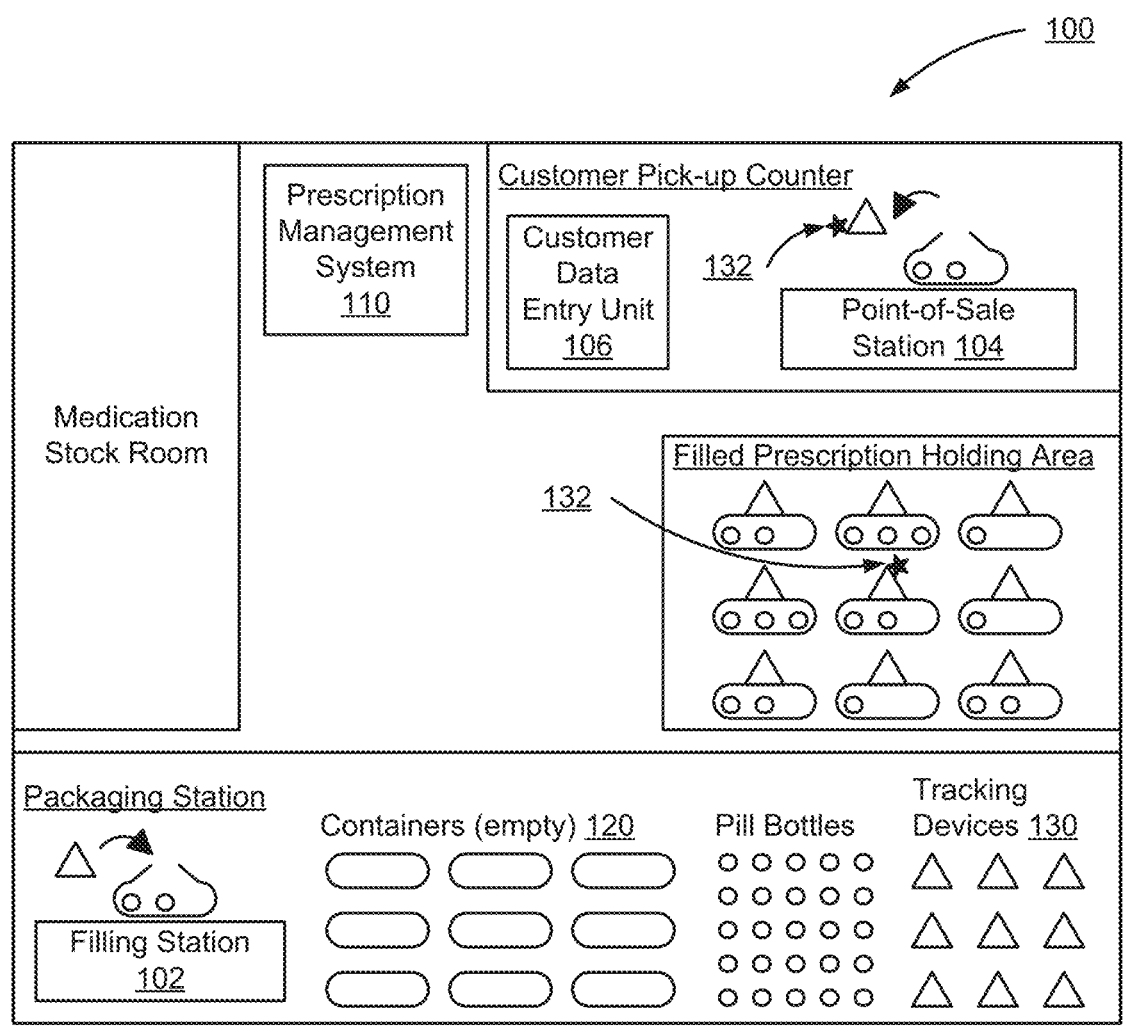
FIG. 1 shows one embodiment of a pharmaceutical environment using a prescription management system.

FIG. 1 shows one embodiment of a pharmaceutical environment 100 using a prescription management system 110. The prescription management system 110 may be a separate or combined system with other management systems, and may reside locally in the store or at a remote location. The prescription management system 110 receives prescription information and manages containers 120 filled with the prescription. The prescription management system 110 receives an indication from a pharmacist or the prescription management system 110 that a particular container 120 is filled with a prescription. The pharmacist stores the container 120 in the pharmacy and, when the prescription is ready to be dispensed to a customer, the prescription management system 110 activates an indicator 132 on the container 120. The indicator 132 is an audio, visual, or other sensory signal that is used to identify the desired container 120. In one embodiment, prior to dispensing the prescription to the customer, information stored on the container is verified with the prescription information received by the prescription management system 110 to ensure the correct container was retrieved. The pharmaceutical environment 100 includes a medication stock room, a packaging station, a filled prescription holding area and a customer pick-up counter.

The packaging station includes a filling station 102, a plurality of tracking devices 130, a plurality of pill bottles, and a plurality of empty containers 120. At the filling station 102, the plurality of empty containers 120 are filled with the pharmaceutical(s) corresponding to a prescription. The pharmaceuticals may be a pill, capsule, tablet, inhaler, injectable medication, cream, salve, and any other item prescribed to a customer. The filled containers 120 are attached to one of the plurality of tracking devices 130, such as through a clipping mechanism, adhesive, or mating components. In another embodiment, the tracking device 130 is a part of the container 120. In other embodiments, the tracking device 130 is placed in the container 120.

In one embodiment, the prescription management system 110 is configured to detect a battery level of the power source of the tracking device 130 and alert a user if the battery level is below a certain threshold. In one embodiment, the tracking device 130 is configured to check its own battery level and alert a user if the battery level is below a certain threshold. In one embodiment, a user may push a button that requests the tracking device 130 to provide a status of the battery level. The tracking device 130 may include an indicator configured to indicate the battery level. This may be performed before or after the tracking device 130 is attached to a filled container 120.

When the prescription is filled at the filling station 102, the filling station 102 transmits a prescription identifier and a tracking device identifier associated with the filled prescription to the prescription management system 110. The prescription management system 110 associates the tracking device identifier with the filled prescription. In one embodiment, when tracking the prescription order, the prescription management system identifies the tracking device 130 holding the prescription by looking up the tracking device identifier and comparing the tracking device identifier with the information of the associated filled prescription information.

In one embodiment, the prescription management system 110 programs the tracking device 130 to store a prescription identifier. In this embodiment, the tracking device 130 is programmable to store the prescription identifier to a local memory. In one embodiment, the tracking device is signaled to receive the prescription identifier. That is, the tracking device may be dormant, in a low power mode, or in a mode not capable of receiving the prescription identifier. In another embodiment, the signal triggers the tracking device to listen to for the prescription identifier. The tracking device may be signaled by various methods, such as a press of a switch, a specific movement such as shaking, a flash of a light, an inductive impulse, a radio frequency signal, electrical contact, or other means. The prescription identifier may include a reference number of the prescription filled in the container 120, customer information, such as a customer's name, address, date of birth, personal identification number (PIN), code of a customer loyalty card, driver's license number, credit card number, or other identifying information. In one embodiment, the tracking device 130 does not store any personally identifiable information. In other embodiments, the tracking device 130 stores information similar or identical to the identifying information on a label of the prescription order of the contents in the container 120. In additional embodiments, the container 120 is already programmed with an identifier and the prescription management system 110 stores an association of the programmed identifier of the container 120 with the customer information. Thus, the prescription management system 110 can verify the prescription order and customer by scanning the container 120.

In one embodiment, the prescription management system 110 sends additional commands to the tracking device 130 when the container 120 is filled. One additional command includes a lock command to lock the container, for embodiments where the containers 120 include locking mechanisms. In another embodiment, there is a sensor system, such as a proximity sensor or magnetic sensor, located on the container 120 that recognizes when the handles have been closed. In this embodiment, the container 120 locks as a result of the handles being closed.

The filling station 102, the point-of-sale station 104, and prescription management system 110 communicate with the tracking device 130 using a wireless communication protocol, such as the Wireless Application Protocol (WAP). In other embodiments, the prescription management system 110 communicates with the container 120 through other wireless communication protocols, including the Worldwide Interoperability for Microwave Access (WiMAX), Global System for Mobile Communications (GSM), 802.11 standards of the Wireless Local Area Network (WLAN), Wireless Personal Area Networks (WPAN), Bluetooth, or Infrared Data Association (IrDA).

In other embodiments, communication is achieved through a physical connection with the filling station 102 and the point-of-sale station 104. The physical connection can be through mounting the container 120 on a rod attached to the station, a bin attached to the station, or a power charge pad on the station.

When a container is filled, the pharmacist adds the container 120 to the filled prescription holding area. Generally, the filled prescription holding area is a rack or a plurality of will call bins. Since there are power sources in the tracking devices 130, such as an internal battery, super capacitor, or other power storage mechanism, which may be rechargeable or replaceable, the filled prescription holding area may not be connected to a power source.

In the embodiment where the power source in the tracking devices 130 is rechargeable, the tracking devices 130 can be recharged through a physical connection with the filling station 102 and the point-of-sale station 104. The physical connection can be through mounting the container 120 on a rod attached to the station, a bin attached to the station, or a power charge pad on the station, powered through conduction, through induction, or by motion. In another embodiment, the container includes a photovoltaic (solar/indoor light) component.

In one embodiment, a prescription may be tracked as the prescription is being filled and stored in a container 120. For example, a user may place a tracking device 130 onto a container 120 and transmit a prescription identifier to the tracking device 130 such that the tracking device 130 and container 120 are associated with a specific prescription. A user may then place an empty medication container, a prescription label, a patient information label, or some combination thereof into the container 120. A user may locate a stock medication container of medication for filling the prescription indicated on the prescription label. The user may then fill the empty medication container in accordance with the prescription information on the prescription label. A user may perform a verification process to verify that the medication matches the prescription information (e.g., in terms of medication type and/or quantity). In some embodiments, the verification process may be performed by an automated system such as a pill identification and/or verification system. Once the prescription is verified, the user may place the container 120 with the filled prescription in a filled prescription holding area. In some embodiments, the prescription management system 100 may record that the filled prescription has been verified. In some embodiments, the container 120 and/or the tracking device 130 may include a sensor for detecting a correct formulation or preparation of the medication. In these embodiments, the container 120 and/or the tracking device 130 may be configured to transmit an alert to the prescription management system 110 to alert a user if a formulation and/or preparation of a medication is incorrect. The steps may be performed in sequence by one or more users (i.e., an assembly line). Example techniques for such medication identification are discussed in applications PCT/US2011/027586 and PCT/US2013/022754, each of which are incorporated by reference in their entireties.

In one embodiment, rather than being filled at the filling station 102, the container 120 is filled with the prescription at a remote location, such as a central pharmacy, where the container 120 is filled with the prescription. The tracking device 130 may be associated with the prescription or programmed with prescription information or prescription identifier at the remote pharmacy rather than at the local pharmacy 100. In one embodiment, when the tracking device 130 arrives at the pharmacy 100, the prescription management system 110 receives a prescription identifier or a tracking device identifier from the tracking device 130. The prescription management system 110 registers the prescription as being received in the store and associates the prescription with the tracking device identifier. In one embodiment, the prescription management system 110 uses the prescription information or prescription identifier in the tracking device to identify the prescription or to add customer information relating to the prescription. This system allows remote filling of a prescription and a quick association of the tracking device within the local pharmacy 100. In the embodiment where the container 120 includes a locking mechanism, the container 120 may also be securely locked during transport.

In one embodiment, a plurality of containers 120 that have been filled with a prescription at the remote location may be sorted for shipment according to the pharmacy to which each container 120 is to be delivered. Each shipment of containers 120 may include a corresponding manifest that details information associated with each container in the shipment, such as the filled prescription, the tracking device identifier, or the prescription identifier. The manifest may be transmitted to the receiving pharmacy prior to the shipment delivery. Additionally, notifications may be sent to customers of the filled prescriptions informing them of when to expect their prescription to be available for pick-up at the pharmacy. Upon arrival of the shipment of containers 120 at the pharmacy, the prescription management system 110 may detect the presence of the tracking devices attached to the plurality of containers 120 and automatically check-in the associated containers 120 according to the manifest. In some embodiments, the tracking devices 130 on the containers 120 may be configured to send an alert to the prescription management system 110, notifying the system of their presence of the respective tracking device. Automatic check-in of containers 120 may beneficially allow a customer to pick up a prescription without further processing at the pharmacy, such as individualized review by the pharmacist. Once a shipment is received, the prescription management system 110 determines whether all of the containers 120 are present (i.e., if any are missing) in the shipment or if there are any additional containers 120 that are not indicated on the manifest (i.e., incorrectly delivered). Once a container 120 is detected, the prescription management system 110 may automatically send a notification to the customer of the associated prescription that the prescription is ready for pick-up. If any containers 120 are missing, the prescription management system 110 may flag the associated prescriptions for a user, wherein the user may choose to notify the customer(s) of the missing prescription(s) that there will be a delay in the availability of the prescription or the prescription management system 110 may automatically send the notification. If any containers 120 are incorrectly delivered, the prescription management system 110 can identify the containers 120 for return shipment to the remote facility. In some embodiments, a barcode associated with the shipment may be scanned to alert the prescription management system 110 that the shipment of containers 120 has arrived at the pharmacy.

In one embodiment, the filled prescription holding area includes a plurality of guidepost stations (not shown) placed in the filled prescription holding area. The guidepost stations include locating features, such as a visual or auditory alarm, that are activated when an indicator 132 on a nearby container 120 is activated.

The customer pick-up counter includes a customer data entry unit 106 and a point-of-sale station 104. The user receives customer data and verifies the customer at the pick-up counter is permitted to be dispensed the prescription retrieved by the user, such as a pharmacist, cashier, or worker. The user receives customer information from the customer directly, through the customer data entry unit 106, which may be a keypad, touch-screen, card reader, a register, a near-field communication device, and any other suitable device for obtaining information from a customer. In one embodiment, the prescription management system 110 sends a wireless command to the associated tracking device 130 using the prescription identifier or the tracking device identifier. The tracking device 130 activates the indicator 132 on the container 120 associated with the customer. The user identifies the container 120 containing the desired prescription using the active indicator 132, and retrieves the associated container 120 from the filled prescription holding area.

In one embodiment, a customer may receive a notification (e.g., via text message, push notification, etc.) when a prescription has been filled and is ready for pick-up. The notification may include a code for scanning (e.g., barcode, QR code, etc.) at the point-of-sale station 104 that allows the user to streamline the pick-up process. The code may be a unique code that identifies the customer or the prescription(s) associated with the customer and can be used to verify the customer's identity for the prescription. The customer may receive the notification on a personal device (e.g., cellular phone, tablet, smartwatch, etc.). In one embodiment, scanning the code at the point-of-sale station 104 triggers the prescription management system 110 to send a wireless command to one or more tracking devices 130 associated with the customer or the prescription(s). The tracking device 130 activates the indicator 132 on the container 120, allowing the user to identify the container 120 containing the desired prescription using the active indicator 132 and retrieve the associated container 120 from the filled prescription holding area.

In some embodiments, the customer may receive one or more suggestions on their personal device. The suggestions may include items for purchase that are available online or at the pharmacy. The items may be related to the prescription that the customer is picking up and/or the items may be historically purchased by other customers purchasing the same or similar prescription to the customer. For example, if a customer is picking up a prescription for cold medicine, suggested items may include cough drops, tissues, a thermometer, tea, juice, etc. In some embodiments, the suggestions may be presented to the customer at the point-of-sale station (e.g., via a display, on a printed receipt, or similar).

In embodiments where the tracking device 130 maintains a prescription identifier, during verification at the point-of-sale station 104, prescription information stored at the prescription management system 110 is compared through a wireless connection with the prescription identifier stored in the tracking device 130, where the prescription identifier could be stored in volatile or non-volatile memory. The user is notified of the results of the comparison and whether the container 120 selected by the user has prescription information matching the prescription information stored at the prescription management system 110. In one embodiment, the results are shown on a visual display located on the container 120, which may be a display that requires low to no power when maintaining an image, such as an electronic paper or e-paper display. In other embodiments, the results are shown on a visual display on a computer screen at the pick-up counter. This allows the user to determine whether the correct prescription was retrieved from the filled prescription holding area.

In certain embodiments, further verification is performed prior to releasing the prescription in the container 120 to the customer. At the customer data entry unit 106 in the pick-up counter, a customer enters a customer or prescription identifier for a prescription order at the customer data entry unit 106. In this embodiment, the customer's identity is verified in addition to verifying the requested prescription was retrieved from the filled prescription holding area. In one embodiment, the customer enters a customer or prescription identifier using a key pad. In other embodiments, the customer provides the prescription identifier using a magnetic stripe reader, a bar code scanner or a Near Field Communication (NFC)/Radio Frequency Identification (RFID) scanner. In other embodiments, instead of entering additional information for prescription retrieval, the customer is required to receive counseling from the user (i.e., a pharmacist or pharmacy technician) about the prescription in the container. The prescription identifier entered by the customer is compared with the prescription identifier stored in the prescription management system 110 or prescription identifier stored in the tracking device 130 of the retrieved container 120. In other embodiments, the prescription management system 120 automatically sends a command to the container 120 to activate the indicators 132 when the customer enters information in the customer data entry unit 106. In the embodiment where the container 120 is locked, when the verification of the customer from the point-of-sale station is received, an unlock command is sent to the tracking device 130 component of the container 120. In other embodiments, the customer is required to receive counseling of the prescription in the container in addition to or instead of the additional customer verification.

In other embodiments, if the verification fails, because the user retrieves the wrong container 120 or the customer enters the wrong information, the prescription management system 110 transmits a signal to cause the container 120 to emit an audible alert, visual alert, or a combination of the mentioned alerts to notify the user. In some instances, the sale of a prescription may be prevented wherein the prescription management system 110 does not allow a prescription to be dispensed from a retrieved container 120 at the point-of-sale station 104. As one example, a locking mechanism or other security measure on the container 120 may prevent retrieval of the prescription. For example, the prescription management system 110 may detect an event associated with a container 120 that indicates that the filled prescription should not be given to a customer. Example events include that the container 120 has been tampered with, that the filled prescription has not been verified, that the stored medication has been recalled, or that a patient consultation is required before the prescription is released to the customer. Before the prescription can be dispensed from the container 120, a remedial action may need to occur, which is discussed in greater detail with regards to FIG. 9. In some embodiments, if the prescription management system 110 detects an event associated with a container 120, the system 110 may prevent retrieval of the container 120 by not sending a transmission to the associated tracking device, thereby prevent a user from identifying and retrieving the container 120. Similarly, before the transmission is sent to the associated tracking device, a remedial action may need to occur.

Figure 2:
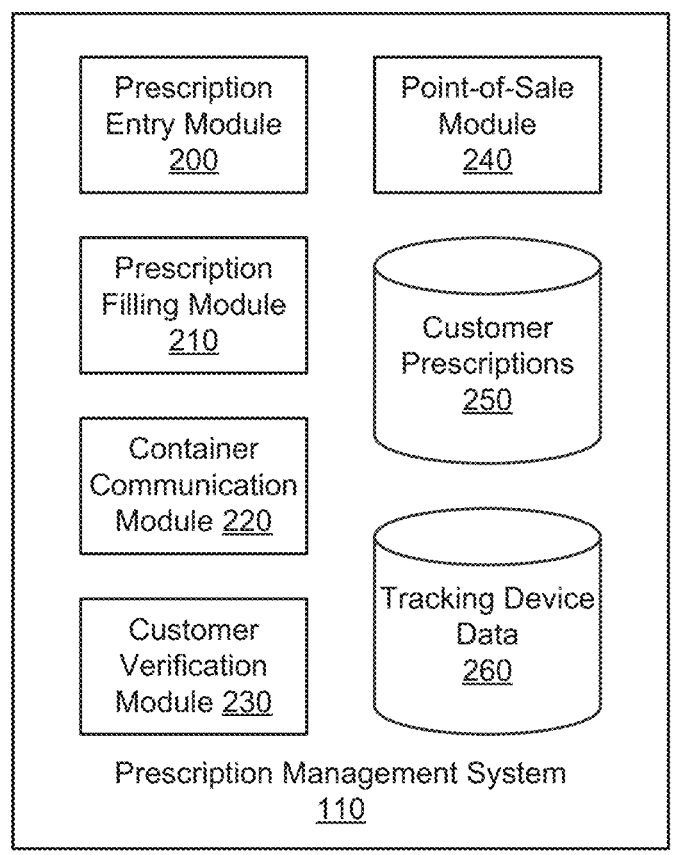
FIG. 2 illustrates components of a prescription management system, according to one embodiment.

FIG. 2 illustrates components of a prescription management system 110 in one embodiment. The prescription management system 110 includes various modules, including a prescription entry module 200, a prescription filling module 210, a container communication module 220, a customer verification module 230, and a point-of-sale module 240 for managing prescription containers. During operation, the prescription management system 120 maintains various data, such as customer prescriptions 250 and tracking device data 260.

Customer prescriptions 250 stores a plurality of prescription identifiers. The prescription identifier may include a reference number of the prescription filled in the container 120, and customer information, such as a customer's name, address, date of birth, personal identification number (PIN), code of a customer loyalty card, driver's license number, credit card number, or other identifying information. In one embodiment, the tracking device 130 stores the prescription identifier. In other embodiments, the tracking device 130 has a pre-programmed identifier.

Tracking device data 260 stores a plurality of tracking device identifiers and an associated plurality of prescription information. The prescription management system 110 associates each tracking device identifier with the respective prescription order, associating each container 120 with a customer.

The prescription entry module 200 manages entry of prescriptions to the pharmacy 100. The prescription management system 110 stores the prescription order and customer information of the prescription identifier into customer prescriptions 122 or sends the information to the customer verification module 230 if the customer information is already maintained in the customer prescriptions 122. The prescription entry module 200 enters a prescription order into customer prescriptions 250 after receiving prescription information. In the embodiment where the prescription order is filled at a remote site, when the container 120 arrives at the local pharmacy 100, the prescription is received by the prescription entry module 200 by various means. In one method, the prescription entry module 200 scans prescription information on the tracking device 130 of the container 120 and queries a remote prescription management system using the prescription information. Once scanned, the prescription entry module 200 files the prescription order into the prescription management system 110. The prescription entry module 200 also compares the shipment of containers 120 to the corresponding manifest to determine that the correct prescriptions are accounted for. Other methods include integrating an additional management system with the local management system, allowing access to the database of the additional management system.

The prescription filling module 210 manages the prescription orders and associates a filled prescription with a tracking device 130. The prescription filling module 210 receives customer information and accesses the customer prescriptions 250 for the prescription order. Once the prescription is placed in the container 120, the prescription filling module 210 receives the tracking device identifier for the tracking device 130 attached to the container 120. The prescription filling module 210 updates the tracking device data 260 with the tracking device identifier and associated prescription information. In embodiments where the tracking device 130 is updated with prescription information, the prescription filling module 210 transmits prescription information to the tracking device 130 through the container communication module 220. In embodiments where the container 120 includes a lock, the prescription filling module 210 transmits a lock command to the tracking device 130 to lock the container 120.

The container communication module 220 relays information and commands from the prescription management system 110 to the tracking device 130 through a wireless transceiver. Once the prescription is placed in the container 120, the container communication module 220 sends the prescription information to the container 120, according to one embodiment. Other embodiments include retrieving a pre-programmed identifier of the container 120. The container communication module 116 may send commands to the container 120 including activating the indicator 132, locking the container 120 once filled, and unlocking the container 120 when retrieved by a customer. In the embodiment where the prescription identifier is stored in the tracking device 130, the container communication module 120 may also read data from the tracking device 130. To address the tracking device 130 on the wireless transceiver, the container communication module 220 transmits the tracking device identifier associated with the desired tracking device 130.

In one embodiment, the container communication module 220 periodically polls each tracking device 130 in the filled prescription holding area to check for its presence. In some embodiments, the container communication module 220 may periodically poll each tracking device 130 to detect a battery level of each tracking device 130. The container communication module 220 may cycle through each tracking device 130 several times a day. The container communication module 220 may ping some tracking devices 130 more often than others, for example, if the associated filled prescription is a high-value drug or a narcotic, or if the filled prescription has been stored in the filled prescription holding area for a long time. In an embodiment in which the tracking devices 132 are in a low power mode, each tracking device 130 may power on at a specific interval to receive the ping from the container communication module 220. Each tracking device 132 may send information to the container communication module 220 in response to receiving the ping. Periodically polling the tracking devices 130 allows the pharmacy to monitor its inventory and prevent theft or tampering with filled prescriptions. In some instances, the container communication module 220 may detect an event associated with a container 120 and will signal to the prescription management system 110 that the container 120 needs to be examined, possibly alerting a user that a remedial action needs to occur, which will be discussed in further detail with regards to FIG. 9. Example events that may be logged by the container communication module 220 include that a container 120 did not respond to a polling signal (e.g., the container 120 is missing or the battery was removed at the time of the polling signal), the container 120 was opened without authorization, or a battery level of a tracking device 130 has dropped below a certain threshold. The detected events may be displayed on a user interface to the user, which may allow the user to locate and retrieve one or more tracking devices 130 with associated events. In some embodiments, a sensor on the tracking device 130 may determine whether the battery level reading is reliable and/or whether or not the container communication module 220 sends a notification to the user regarding the battery level.

The customer verification module 230 receives a prescription identifier from the prescription entry module 200. Once the container 120 is at the point-of-sale station 104 in the customer pick-up counter, the customer verification module 230 retrieves the prescription identifier from the tracking module 130. The customer verification module 230 compares the prescription identifier with the prescription identifier received from the tracking device 130. The prescription management system 110 sends a notification to the user through a visual display indicating whether the prescription identifier matches or does not match the identifier stored on the tracking device 130. In the embodiment where the container 120 was sent a lock command, the customer verification module 230 sends an unlock command responsive to the information matching. In one embodiment, the customer verification module 230 prevents the sale of a prescription by not allowing access into the retrieved container 120 due to a detected event associated with the retrieved container 120. The customer verification module 230 may keep the container 120 locked or may display an on-screen notification to a user that a remedial action is required.

Figure 3:
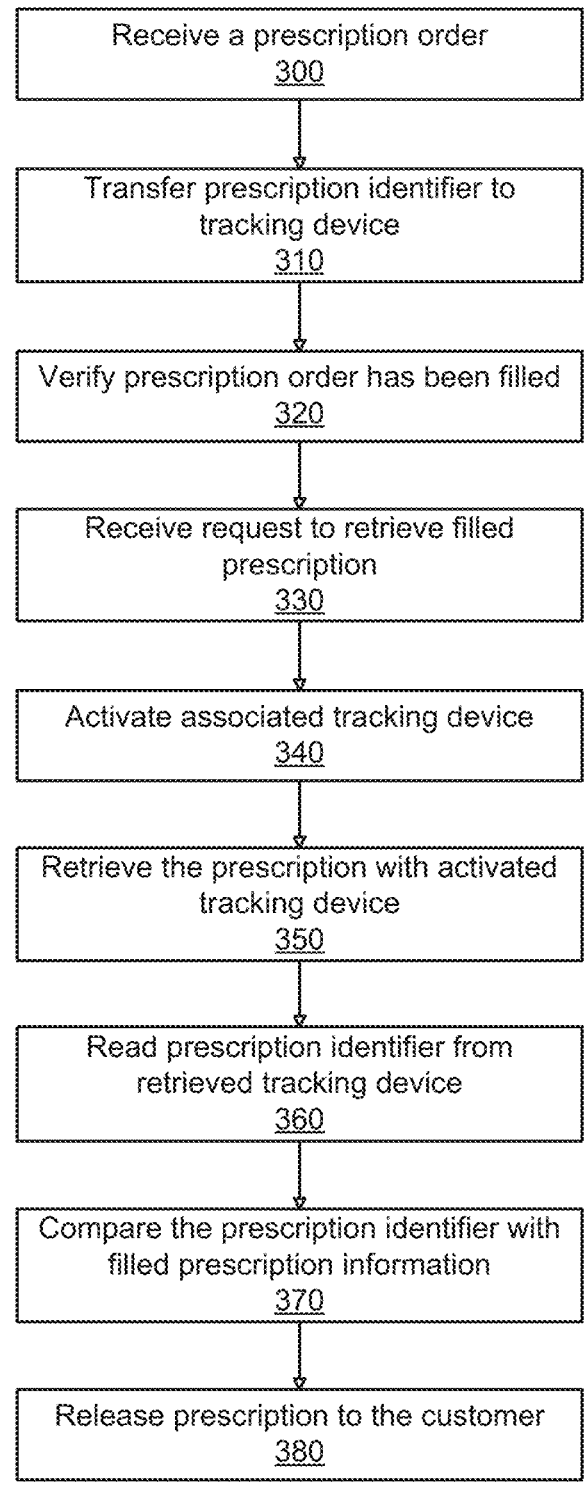
FIG. 3 is a flowchart for tracking a prescription, according to one embodiment.

FIG. 3 is a flowchart for prescription tracking according to one embodiment. This process can be performed by the various modules of the prescription management system 110. First, a prescription order is received 300. The prescription order may come from a customer, a medical practitioner, or a user, such as a pharmacy worker, cashier, or pharmacist. Once the container 120 has been filled with the associated prescription, the prescription identifier is transferred 310 to the container 120. In another embodiment, the prescription identifier includes prescription information. In one embodiment where the prescription order is filled at a remote site, the container 120 is detected or scanned at the local pharmacy to file the prescription order in the local prescription management system 110. The prescription management system 110 optionally verifies 320 the prescription order has been filled.

Next, the prescription management system 110 receives 330 a request to retrieve a filled prescription. The prescription identifier or tracking device identifier associated with the prescription is accessed and the request to activate 340 the associated tracking device is transmitted to the tracking device 130. In one embodiment, the transmission is sent to a channel received by a plurality of the tracking devices 130. In this embodiment, the transmission specifies the prescription identifier or tracking device identifier to be activated, and the tracking devices receive the transmission and determines whether the transmission includes information designating that tracking device, by matching the information to information stored by the tracking device 130. For example, if customer Jack requests his prescription, the prescription management system 110 sends customer information associated with Jack in the activation command. In response, the tracking devices determine whether the transmitted customer information matches the stored customer information in the tracking device. The tracking devices that have customer information associated with Jack will match and activate an indicator.

After activation, a user retrieves the activated container(s) with an activated indicator. The container with the activated tracking device 130 is retrieved 350 by the user. The prescription information on the tracking device 130 is read 360. The prescription management system 110 compares 370 the prescription identifier retrieved from the tracking device with the information of the filled prescription information in the container 120. When the information matches, the user releases 380 the prescription to the customer. In other embodiments, when the information matches, the prescription management system 110 permits access to the container 120 and, in the embodiment where the container 120 is locked, the prescription management system 110 sends an unlock command to the container 120. In one embodiment, the tracking device is cleared of the prescription identifier after the information matches.

Figure 4:
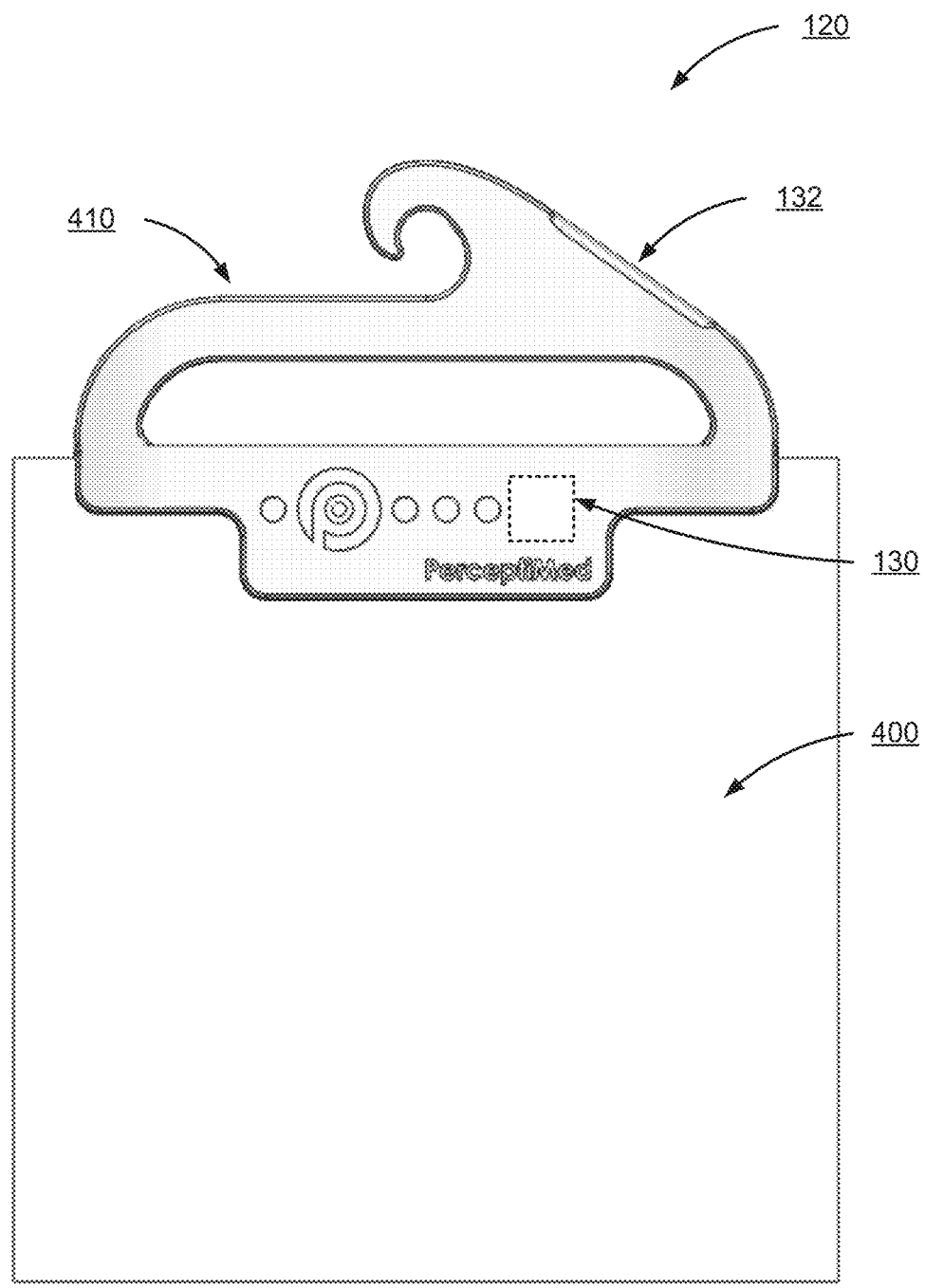
FIG. 4 is one embodiment of a container for holding prescriptions, according to one embodiment.

FIG. 4 is one embodiment of the container 120 for holding prescriptions. The container 120 includes a tracking device 130, an indicator 132, a bag 400, and a handle 410. In this embodiment, the indicator 132 is a visual indicator, e.g., a light emitting diode (LED), which lights a portion of the handle when activated. In other embodiments, the indicator 132 can be alternative visual indicators including multicolor LEDs or other visual displays, auditory indicators including speakers or buzzers, or any other component that sends a sensory cue.

In the embodiment shown in FIG. 2, the bag 400 is a clear plastic bag. In other embodiments, the bag 204 can be made of other durable, reusable materials. Alternatively, the bag 400 may be opaque rather than clear, to prevent light contamination of the prescription and view of the prescription by unauthorized persons. In some embodiments, the bag 400 may be configured to transition between opaque and clear. For example, if a bag 400 storing a prescription is opaque, a user may provide a user input (e.g., button press, flip switch, or similar methods) that causes the bag 400 to become clear such that the user is able to see the stored prescription. This may enable the user to read the prescription label, confirm the stored prescription, confirm the customer associated with the stored prescription, check for an expiration date or a fill date, or some combination thereof. An additional user input may cause the bag 400 to revert to opaque. In some embodiments, the degree of opacity may be adjusted by the user. In one embodiment, the bag may use electronic paper display technology (i.e., electronic ink) to display information regarding the stored prescription. The electronic ink may be configured to erase information if the tracking device 130 detects an event (e.g., tampering, removing the battery, etc.).

The handle 410 is made of two mating sides that are detachable from one another. In embodiments where the handle 410 is a clip mechanism, the two mating sides may or may not be detachable from another, depending on the hinge of the clip mechanism. The bag 400 has an open side that is attached to the mating sides of the handle 410. When the mating sides of the handle are mated with one another, the bag 400 is closed and, in other embodiments, is locked. In the embodiment shown in FIG. 4, the handle 410 comprises a hook shape with a grip area. In other embodiments, the handle 410 does not have a hook or grip. In the embodiment of FIG. 4, the hook of the handle 410 beneficially allows the container 120 to be suspended in the filled prescription holding area. The hook configuration allows a user to place the container 120 at any location rather than having the container 120 associated with a specific location, wherein the relationship must be stored by the prescription management system 110, and introducing the possibility of human error if a user places the container 120 in the wrong location.

Figure 8:
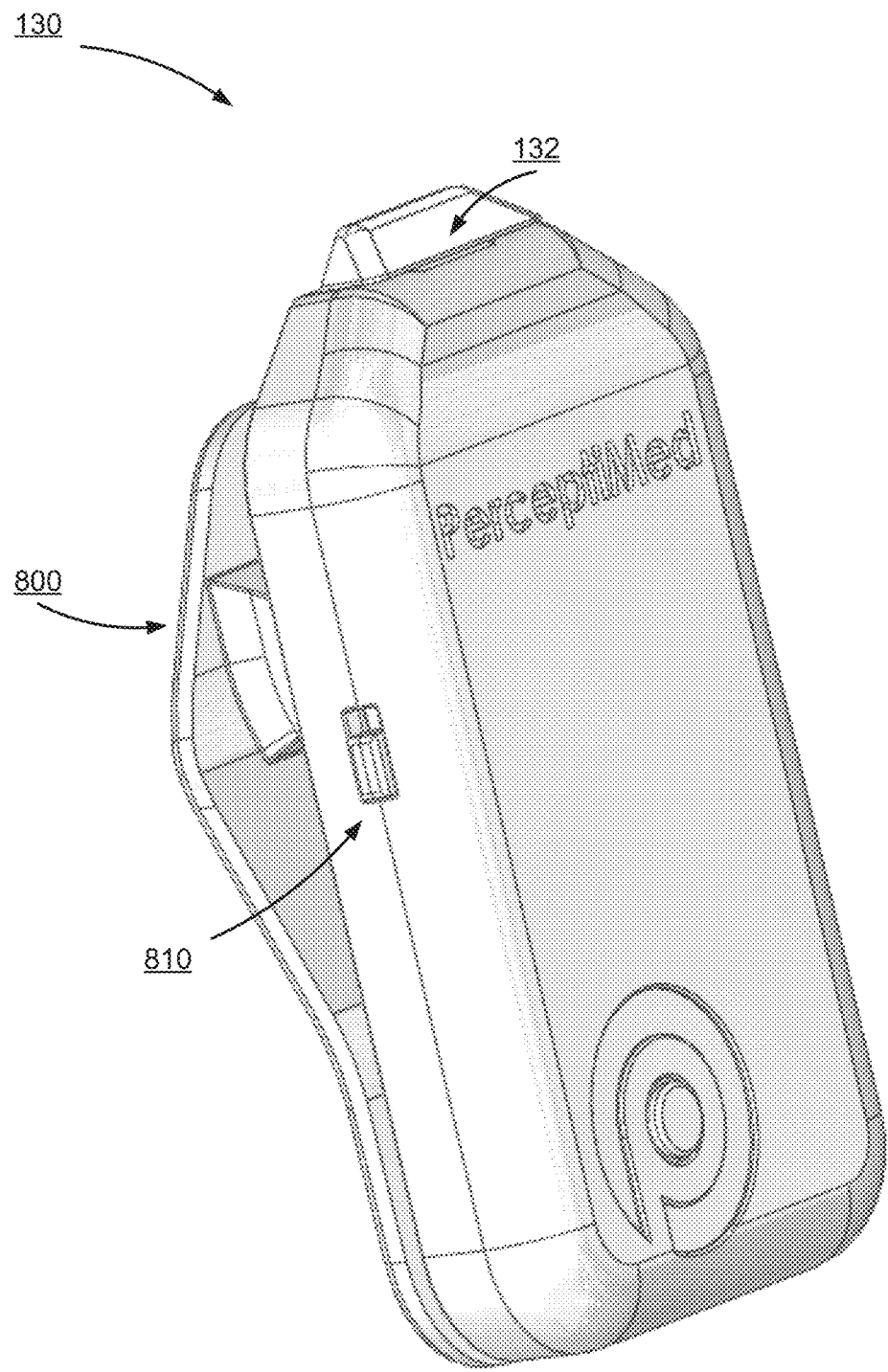
FIG. 8 shows a detachable tracking device, according to one embodiment.

In the embodiment shown in FIG. 4, the tracking device 130 is enclosed within the handle 410. In other embodiments, the tracking device 130 may be a detachable or mountable component. In other embodiments, the tracking device 130 and locking mechanism are mechanically integrated into one component. One embodiment of a detachable tracking device 130 is shown in FIG. 8.

In one embodiment, the container 120 includes additional components not shown in FIG. 4. Such components include a locking closure mechanism, a motor that controls the locking closure mechanism, a display panel, a tracking device identifier and a station connector. The motor that controls the locking closure mechanism drives the mechanical mechanism for locking and unlocking the container 120. In one embodiment, the tracking device identifier is a fixed code assigned to each container 120, such as a RFID tag. The display panel is a low-power-consumption or no-power-consumption display, such as an e-paper display, and shows the prescription identifier stored on the tracking device 130.

The container 120 and/or the tracking device 130 may include one or more sensors. In one embodiment, one of the sensors is a temperature sensor for monitoring a temperature of an environment in which the filled prescription is held. In one embodiment, one of the sensors is a humidity sensor for detecting a level of humidity in the environment. The tracking device 130 may be programmed to store a specified temperature range and/or humidity range in which the medication in the container 120 should be stored. The tracking device 130 may be configured to store a log of temperature and/or humidity data, which the tracking device 130 can report to the prescription management system 110. The tracking device 130 may be configured to transmit an alert to the prescription management system 110 if one or more sensors detects a temperature and/or humidity level outside of the corresponding specified range for the medication. The tracking device 130 may transmit the alert if one or more sensors detects a temperature and/or humidity level outside of the corresponding specified range for the medication for a certain amount of time. In one embodiment, the prescription management system 110 prevents a prescription associated with a sensor alert from being sold to a customer. The prescription management system 110 may prevent retrieval of the tracking device 130 in response to a broadcasted request associated with a customer. The prescription management system 110 may prevent retrieval by erasing customer-specific information stored on the tracking device 130, by blocking a broadcast request for the filled prescription, by not activating an indicator on the tracking device 130 in response to a broadcasted request, or some combination thereof. The prescription management system 110 may allow retrieval of the tracking device 130 in response to a user locating the tracking device 130 to verify or replace the filled prescription.

Figure 5:
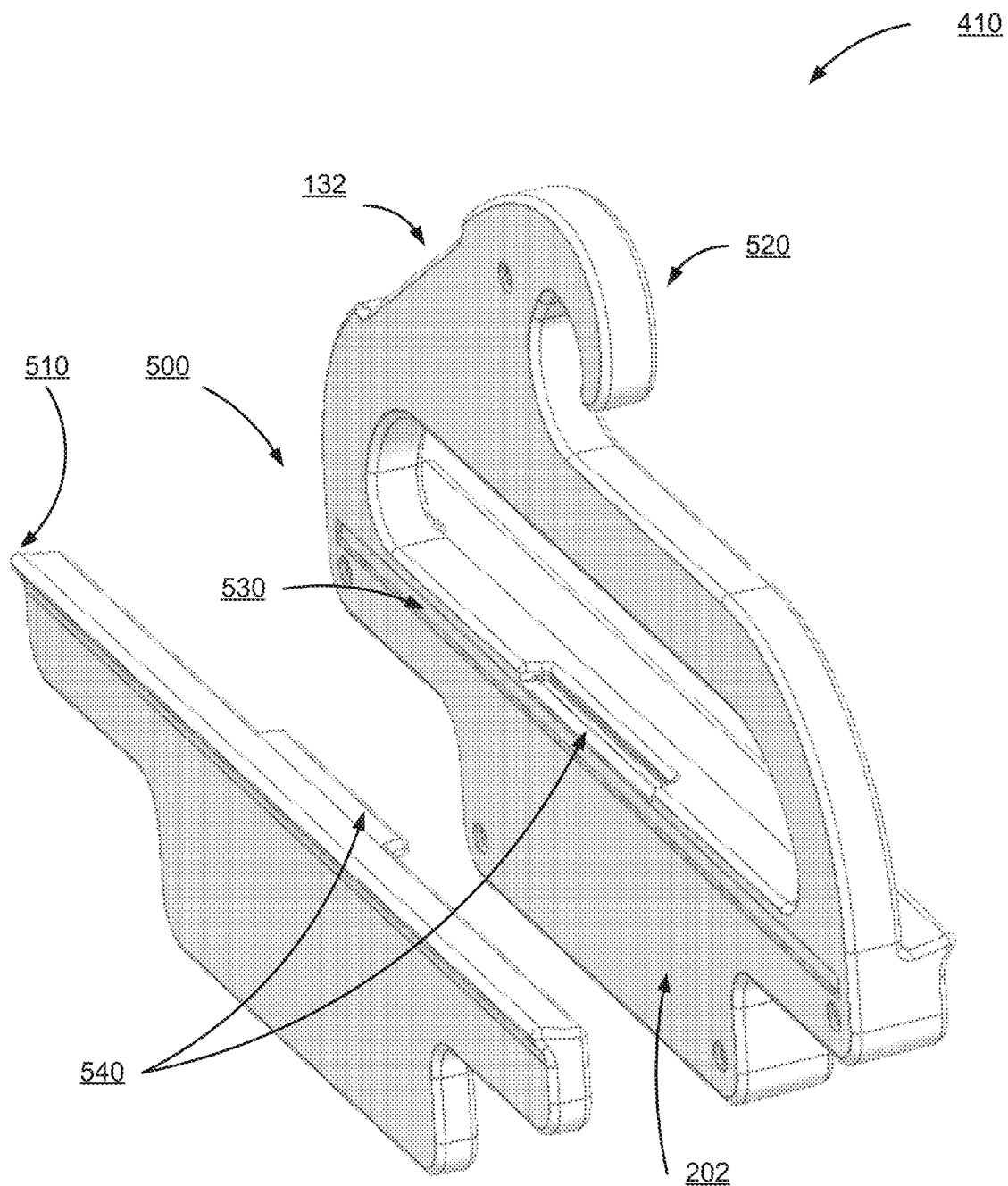
FIG. 5 is a perspective view of components of a handle for a prescription container, according to one embodiment.

FIG. 5 is a perspective view of the handle 410 according to the embodiment shown in FIG. 4. In one embodiment, the handle 410 includes a main closure mate 500 and a complementary closure mate 510, a hook 520, one or more indicator sources 132, a coupling groove 530, and a closure mechanism 540.

In one embodiment, the handle 410 includes a hook 520 in a curved C-shape. In other embodiments, the hook 520 has alternative forms, such as a T-shape, O-shape or an oval opening.

The main closure mate 500 and complementary closure mate 510 attach to the open ends of the bag 400 at the coupling groove 530 and close the open ends of the bag 400 when the mates are joined.

The handle 410 has the coupling groove 530, which is an indentation along the handle 206. The coupling groove 304 couples the bag 204 to the handle 410 using adhesives lined along the coupling groove 304, attached to the open ends of the bag 400. In other embodiments, other attachments join the bag to the coupling groove 304, such as a hook-and-loop connection, buttons, matching male and female mates, a zipper, or any other means to create a connection. In alternatives, the bag is joined to each mate using structures other than the coupling groove 530, including slide joints, twist joints or other mechanical connection joints.

The handle 410 is closed at least in part by the closure mechanism 540. In the embodiment shown in FIG. 5, the closure mechanism 540 comprises a lip located on the complementary closure mate 510 and a lip hook on the main closure mate 500. The closure in this embodiment joins the closure mates and prevents the complementary closure mate from sliding downward relative to the main closure mate (which is typically suspended by the hook). In other embodiments, the closure mechanism 540 is a Velcro connection, a plurality of one or more buttons, a plurality of one or more matching male and female mates, a zipper, a magnet, or any other means to join the closure mates.

Figure 6:
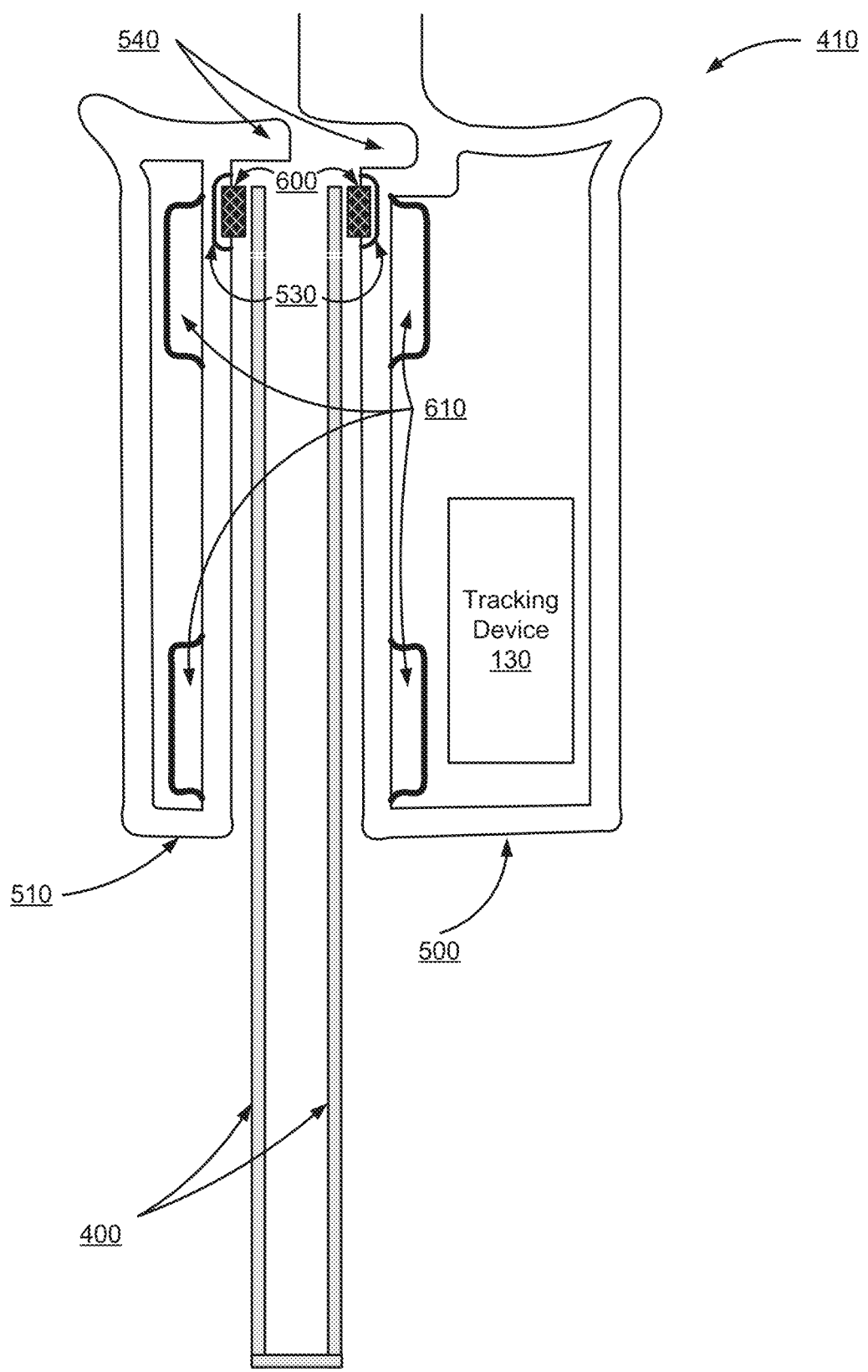
FIG. 6 is a cross-section view of a handle for a prescription container, according to one embodiment.

FIG. 6 is a cross-section view of the main closure mate 500 and the complementary closure mate 510 shown in the embodiment in FIG. 4. A set of adhesives 600 fit into the indentation of the coupling groove 530 and couples the open ends of the bag 400 with the main closure mate 500 and complementary closure mate 510. In addition to the closure mechanism 540, additional force for closing the bag 400 is provided by two sets of complementary magnets 610 enclosed in the closure mates 500, 510. The magnets 610 and closure mechanism 540 maintain the bag 400 in a closed state and prevent the closure mates from leaving contact with one another. In this embodiment, the tracking device 130 is stored in the main closure mate 500.

While described with respect to certain embodiments, the handle 410 in additional embodiments has variations. For example, the closure mechanisms may include different closures, such as snaps, mating plastic inserts, hook-and-loop structures, and various other connections. In addition, while the main closure mate 500 and the complementary closure mate 510 are shown herein as disproportionate in size, the size of each closure mate may be equal, or the complementary closure mate 510 may be larger than the main closure mate 500. Likewise, while the closure has been shown here at the base of the handle, the closure in certain embodiments may be located at the top of the handle, such as near the hook. In addition, while the closure has been shown as a connection of the inside facing sides of the closure mates, the closure in other embodiments is through closure mechanisms connected to the outside facing sides of the closure mates, such as a grip clip, strap, slide clips or other clipping mechanisms.

Figure 7:
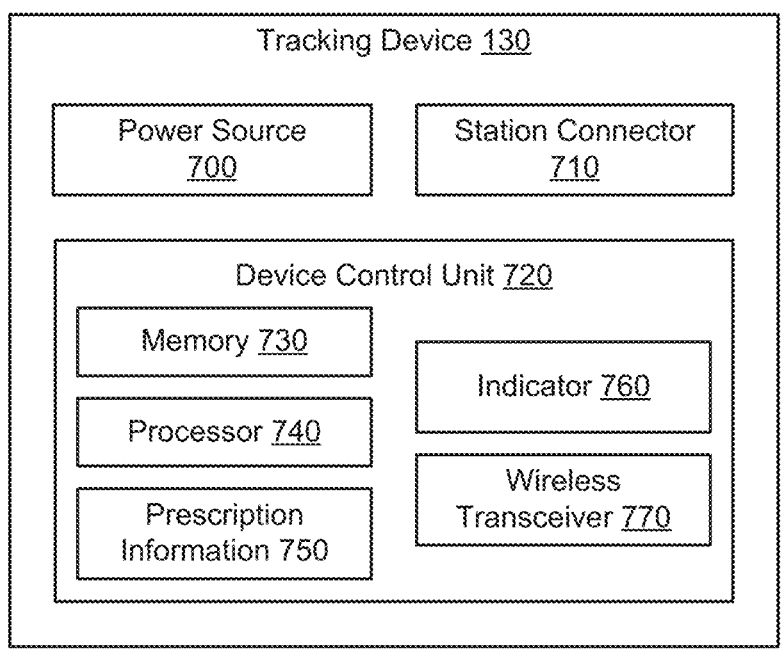
FIG. 7 is a block diagram of a tracking device, according to one embodiment.

FIG. 7 is a block diagram of a tracking device 130 according to one embodiment. The tracking device 130 may be enclosed within a container 120 or may be attachable or mountable to the container 120. The tracking device 130 includes a power source 700, a station connector 710, and a device control unit 720. The power source 700 can be an internal battery, super capacitor, or other power storage mechanism, which may be rechargeable or replaceable. In the embodiment of a rechargeable power source 700, the tracking device 130 can be recharged by coupling with the container 120 with the filling station 102 or the point-of-sale station 104 through a station connector 710. The station connector 710 can be a physical connector mounting the container 120 on a rod attached to the station, a bin attached to the station, or a power charge pad attached to the station, powered through conduction, through induction or by motion. In another embodiment, the container is powered by a photovoltaic (solar/indoor light) component.

The device control unit 720 includes a memory 730, a processor 740, at least one indicator 760, and a wireless transceiver 770. The memory 730 stores instructions and data that may be executed by the processor 740. In one embodiment, the memory 730 stores identifiers as well. Memory 730 may be a dynamic random access memory (DRAM) device, a static random access memory (SRAM) device, Flash RAM or other non-volatile storage device, combinations of the above, or some other memory device known in the art. In one embodiment, the at least one indicator 760 includes an LED indicator. In other embodiments, the indicator 760 can be other visual indicators including multicolor LEDs, visual displays, etc., auditory indicators including speakers, buzzers, etc., or any other component that sends a sensory cue. In one embodiment, the wireless transceiver 770 is the method of communication with the prescription management system 110. Other wireless communication protocol embodiments the Worldwide Interoperability for Microwave Access (WiMAX), Global System for Mobile Communications (GSM), 802.11 standards of the Wireless Local Area Network (WLAN), Wireless Personal Area Networks (WPAN), Bluetooth, or Infrared Data Association (IrDA). In one embodiment, the device control unit 720 includes a locking mechanism. Thus, in the embodiments where the container 120 includes the locking mechanism, the prescription management system 110 sends a lock command to the device control unit 720. Additional embodiments include a low-power-state feature. This feature allows the containers 120 to remain in a low-power state and require low to no power when stored away and not actively communicating with the prescription management system 110. In one embodiment, the tracking device is signaled to receive or transmit by the press of a switch, a specific movement such as a shaking, a flash of a light, inductive impulse, radio frequency signal, electrical contact, or other such method for activation. The activation signals the tracking device 130 to receive an identifier for storage.

In the embodiment where the containers 120 include locking mechanisms, the complementary components for the locking mechanism would be located on the main closure mate and complementary closure mate of the container handles (not shown). In one embodiment, the lock mechanism would be an electric lock using magnets, also known as a magnetic lock where the prescription management system 110 would actuate the lock by either supplying or removing power. In other embodiments, the electric lock mechanism would use solenoids or motors where the prescription management system 110 would actuate the lock by either supplying or removing power. Other embodiments of lock mechanisms include the prescription management system 110 reading a Radio Frequency Identification (RFID), requiring a numerical keypad, reading a security token swipe, scanning fingerprints or retinas, and identifying voiceprints. Additional embodiments include the user informing or counseling the customer of the prescription in the container 120. Other embodiments include having the user request additional verification information from the customer, such as a customer's name, address, date of birth, personal identification number (PIN), code of a customer loyalty card, driver's license number, credit card number, an answer to a private security question, or other identifying information.

In the embodiment where the containers 120 include locking mechanisms, the indicator 132 on the container 120 can be a multicolor LED that indicates the status of the lock through the color of the multicolor LED. For example, a locked container may have the multicolor LED flash red and an unlocked container may have the multicolor LED flash green. In additional embodiments, the electronic lock requires low or no power when locked.

In other embodiments, the prescription management system 110 programs the tracking device 130 through the device control unit 720 to store a prescription identifier. In this embodiment, the tracking device 130 is programmable, where information or identifiers can be stored on or removed from local memory 730. In other embodiments, the prescription management system 110 retrieves a pre-programmed identifier on the tracking device 130 through the device control unit 720. In one embodiment, the prescription identifier includes personally identifiable information. In another embodiment, the prescription identifier does not include personally identifiable information but stores information similar or identical to the identifying information on a label of the contents or the prescription order in the container 120.

In other embodiments, the device control unit 720 receives commands from the prescription management system 110 to activate the indicator signals on the container 120 and sends commands to the indicator signals to activate. The indicator signals include visual indicators, such as a LED, which lights a portion of the handle when activated. In other embodiments, the indicator signals can be visual indicators including multicolor LEDs or other visual displays, auditory indicators including speakers or buzzers, or any other component that sends a sensory cue.

FIG. 8 shows one embodiment of a detachable tracking device 130. The detachable tracking device 130 includes a power source 700 and a device control unit 720 as described above. The detachable tracking device 130 includes an attachment mechanism 800 in the form of a clip for attaching to a container 120. In one embodiment the clip of the detachable tracking device 130 includes a sticky, adhesive, or high-friction surface to prevent the clip from sliding off a container or other object attached by the clip. In one embodiment, the detachable tracking device includes a hook in a curved C-shape. In other embodiments, the hook has alternative forms, such as a T-shape, O-shape, or an oval. In one embodiment, the detachable tracking device is signaled to receive or transmit by an activation as described above. The detachable tracking device 130 may include a power switch 810 for energy efficiency. The detachable tracking device 130 also includes an indicator 132, which may be visual, such as an LED, multicolor LED, or other visual display, or auditory, such as a speaker or buzzer, or any component that sends a sensory cue.

In one embodiment, a plurality of one or more users may retrieve a plurality of one or more containers 120 at the same time using tracking devices 130 including multicolor visual indicators, with each color indicating a different customer's prescription. For example, if a plurality of one or more users requests a plurality of one or more customer's prescriptions, the prescription management system 110 sends a command to a plurality of tracking devices 130 attached to the plurality of one or more containers 120 to activate a different color for each customer. Then, the prescription management system 110 notifies the plurality of one or more users of the color associated with the requested containers 120.

In another embodiment, if a user in a plurality of one or more users is retrieving multiple prescriptions for one customer, the prescription management system 110 activates each tracking device belonging to the customer in a single LED color, allowing the user to retrieve multiple prescriptions belonging to the customer at once by selecting the tracking devices of that color. In the embodiments above, the prescription management system 110 maintains a record of the colors currently activated on at least one tracking device and selects a color to activate from colors that are not currently active.

In another embodiment, customers may sign up to receive their prescription(s) via home delivery. As a filled prescription is stored in a container 120 with a tracking device 130 (at the pharmacy or at a remote location), the tracking device 130 may store an indication that the customer associated with the filled prescription is signed up to have the prescription delivered to their home rather than be picked up at the pharmacy. The prescription management system 110 and/or the tracking device 130 may store a scheduled home delivery date or an address to which the prescription is to be delivered. The prescription management system 110 facilitates the process of home delivery by allowing a user to quickly locate all of the prescriptions stored in the filled prescription holding area that are flagged for home delivery. A user (e.g., a pharmacist, a technician, or a delivery person) may request the prescription management system 110 to send a request to tracking devices 130 that are marked for delivery. The request may specify a delivery date or a delivery route or delivery region that specifies an area or a zip code to which the delivery person is planning to deliver. In one embodiment, the prescription management system 110 may identify specific tracking devices associated the delivery date, route, or region of the request and broadcast the associated tracking device identifiers. The prescription management system 110 may directly transmit the tracking devices identifiers to the corresponding tracking devices or may broadcast the tracking device identifiers to a plurality of tracking devices, such that the tracking devices compare the broadcasted tracking device identifiers to a stored tracking device identifier. Responsive to a match between the received identifier and the stored identifier, one or more tracking devices may activate their respective indicators 132. In another embodiment, a plurality of tracking devices may receive the request specifying the delivery date, route, or region, and then perform a comparison to information stored on the tracking device. Responsive to a match between the received information and the stored information, one or more tracking devices may activate their respective indicators 132. As a result, only tracking devices 130 associated with prescriptions for customers living within the delivery region and/or are scheduled for delivery on a specific date will activate its indicator 132. The user may locate the containers 120 having activated tracking devices 130, allowing the containers 120 to be loaded for delivery (e.g., into a delivery truck). In some embodiments, the prescription management system 110 may determine if all prescriptions flagged for home delivery have left the pharmacy (i.e., have been loaded into the delivery truck) and if the presence of the associated tracking devices are no longer detected within the filled prescription holding area. If the prescription management system 110 detects that one or more tracking devices flagged for home delivery are still present within the filled prescription holding area, indicating that one or more prescriptions have been left behind, the system 110 may send a notification to the user (via an on screen alert at the point-of-sale station 104) and/or the delivery person (via a push notification), notifying them that a prescription has been missed. This allows the delivery person to return to the pharmacy to retrieve the missed prescription. In some embodiments, a notification may be sent to a customer when the prescription is loaded for delivery to notify the customer that the prescription is on its way.

In one embodiment, a customer may have authorized prescriptions to be delivered via home delivery, but the customer may have indicated a preference to pick up the prescriptions rather than have the prescriptions delivered. In the event that a prescription has been stored in the filled prescription holding area for longer than a designated holding period, the prescription management system 110 may automatically flag the prescription for home delivery if the customer associated with the prescription has authorized home delivery. By converting held prescriptions to delivery prescriptions, the pharmacy is able to prevent prescriptions from sitting in the filled prescription holding area for too long and expiring.

In one embodiment, the tracking devices 130 may be configured to detect its geographical location, e.g., when a container 120 is in a delivery truck out for delivery. In this embodiment, a tracking device 130 may activate its indicator 132 when it detects that it is within a certain proximity to its delivery address, allowing the delivery person to conveniently locate the prescriptions to be delivered at a delivery location. In some embodiments, the delivery truck may have a built-in or transportable system that is able to monitor the geographical location of the truck, such that when the delivery truck is within a certain proximity to a designated delivery address, the system sends a request to the one or more tracking devices 130 in the delivery truck to activate its indicator 132 if the tracking device 130 is associated with a prescription to be delivered at a nearby location. If several prescriptions are to be delivered at locations near to each other, the indicators 132 may light up in different colors to indicate which prescriptions belong to different customers. In some embodiments, when the tracking device is activated at a customer's location for delivery, the geographical location and/or the event of prescription delivery may initiate a request for the customer to confirm receipt of the prescription. The proof of receipt may be obtained via a signature pad.

In another embodiment, all of the prescription orders that have been sitting in the filled prescription holding area for longer than a designated holding period can be indicated at the same time by the prescription management system 110, thus allowing the user to efficiently remove aged or expired prescription orders.

In one embodiment, the prescription management system 110 allows a user to search for filled prescriptions and return them to stock. If a filled prescription has been sitting in the filled prescription holding area for longer than a designated holding period and is not expired, the prescription management system 110 can activate the indicators 132 on those containers 120, allowing a user to efficiently locate the filled prescriptions. As a user performs the return to stock process, a user interface may display the steps of the process, e.g., "Searching," "Located," "Flashing," and "Retrieved," to indicate to a user if any filled prescriptions and associated tracking devices have been identified and if all identified filled prescriptions have been retrieved. This configuration may allow a user to search for a needed medication name or code to identify if there are filled prescriptions having the needed medication and that have been sitting in the filled prescription holding area for longer than a designated holding period. The user can retrieve the containers 120 and convert the filled prescription to a stock bottle that can be used to fill a prescription.

In some embodiments, once a filled prescription is identified by the prescription management system 110 as a prescription that is to be converted to a stock bottle, the prescription management system 110 may prevent retrieval of the filled prescription in response to a broadcasted request associated with a customer. The prescription management system 110 may prevent retrieval by erasing customer-specific information stored on the tracking device 130, by blocking a broadcast request for the filled prescription, by not activating an indicator on the tracking device 130 in response to a broadcasted request, or some combination thereof. In this configuration, the prescription management system 110 prevents the filled prescription from being dispensed to a customer after the filled prescription has been tagged for converting to stock medication. In some embodiments, the prescription management system 110 may automatically print a new label for the filled prescription to designate it as a stock bottle. Printing the new label for the stock bottle ensures that the patient information on the previous label is covered up and/or kept confidential and ensures that the stock bottle is labeled correctly identifying the medication information (e.g., type of medication, strength, expiration date, quantity, etc.) such that the medication can be safely used to fill a prescription of another patient. In some instances, rather than returning the filled prescription to stock, if a customer has authorized prescriptions to be delivered via home delivery and the prescription management system 110 detects that a prescription has been stored in the filled prescription holding area for longer than a designated holding period, the prescription management system 110 may automatically flag the prescription for home delivery. The prescription management system 110 may be configured to detect all filled prescriptions that have been held for longer than a designated holding period and activate indicators 132 on containers 120 for return to stock in a first color and activate indicators 132 on containers 120 for home delivery in a second color.

In some embodiments, the prescription management system 110 sends information that a filled prescription has been returned to stock to an insurance company to reverse any charges (i.e., a customer won't be charged for a prescription that was never picked up). If a user returns a prescription to pharmacy inventory without notifying an insurance company or other third-party payer that the prescription has been returned to stock, then the pharmacy might be paid by the payer for a prescription that was not delivered to a customer. This may cause the pharmacy to be out of compliance, potentially introducing a risk if the pharmacy were to be audited. By automating the process and notifying the insurance company upon retrieval of the prescription to be converted to stock medication, this ensures that the pharmacy remains in compliance and minimizes human error.

In one embodiment, a user may scan a label on a stock bottle into the prescription management system 110. Based on the medication in the stock bottle, the prescription management system 110 may identify which prescriptions are to be filled with the medication. In some embodiments, the unfilled prescription containers may be associated with a tracking device 130 and/or storage container 120. The prescription management system 110 may identify the prescriptions to be filled with the medication and activate an indicator on the associated tracking device 130, enabling a user to locate the prescriptions to be filled. In some embodiments, the indicators on the tracking devices 130 may flash in a specified color such that a user can accurately locate the correct tracking devices 130. In this configuration, a user may fill several prescriptions at once and streamline the prescription filling process.

In one embodiment, if a bad batch of medication has been sent to the pharmacy, the prescription management system 110 identifies prescriptions holding the bad batch and commands the tracking devices 130 associated with the containers 120 holding the medication from the bad batch to activate the indicator signals on the associated tracking devices 130. Thus, the users can quickly remove the faulty prescription from the pharmacy.

Figure 9:
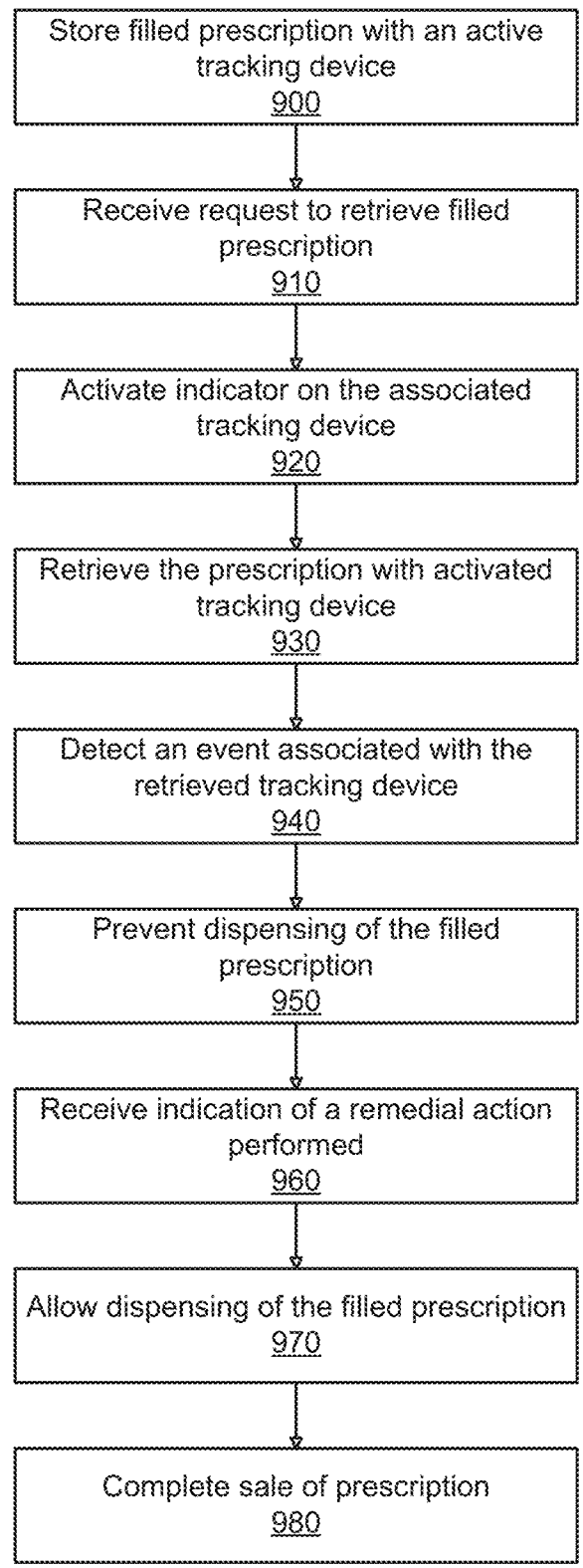
FIG. 9 is a flowchart for preventing sale of a prescription, according to one embodiment.

FIG. 9 is a flowchart for preventing sale of a prescription, according to one embodiment. This process can be performed by the various modules of the prescription management system 110. First, a filled prescription is stored 900 in a container 120 with an active tracking device 130, and the container 120 is placed into a filled prescription holding area. The prescription may have been filled at the pharmacy or at a remote location.

Next, the prescription management system 110 receives 910 a request to retrieve a filled prescription. The prescription identifier or tracking device identifier associated with the prescription is transmitted to the tracking device 130 in the filled prescription holding area. In one embodiment, the transmission is sent to a channel received by a plurality of the tracking devices 130. In this embodiment, the transmission specifies the prescription identifier or tracking device identifier to be activated, and the tracking devices 130 receive the transmission and determine whether the transmission includes information designating that tracking device 130, by matching the received information to information stored by the tracking device 130. In response, the tracking devices 130 that have the matching information will activate 920 an indicator 132.

After activation, a user retrieves 930 the container(s) with an activated indicator 132. The user brings the retrieved container(s) to the point-of-sale station 104 to verify and release the prescription to the customer. However, the prescription management system 110 may detect 940 an event associated with the retrieved tracking device and prevent 950 the prescription from being dispensed to the customer. Example events that the prescription management system 110 may detect include that the container 120 has been tampered with, that the filled prescription has not been verified, or that a patient consultation is required before the prescription is released to the customer. In the embodiment of FIG. 9, a tracking device 130 may be associated with one or more events simultaneously. When the prescription management system 110 detects an event associated with a retrieved tracking device, the prescription management system 110 must receive 960 an indication that a remedial action has been performed before the prescription can be released to a customer.

The prescription management system 110 may detect that a container 120 has been tampered with. Examples of tampering may include opening the container 120 without authorization, removing the battery of the tracking device 130, or removing the container 120 from the filled prescription holding area. One or more of the tampering events may be detected by the prescription management system 110 through its periodic polling. For example, the prescription management system 110 may detect that a container 120 is missing or has had its battery removed if its tracking device 130 does not respond to its polling signal from the prescription management system 110. In some embodiments, a tracking device 130 may be configured to record an event log such as if the container 120 was opened without authorization or if the battery of the tracking device 130 was removed without authorization (the event generated once the battery is replaced). When an event is associated with a tracking device 130, the prescription management system 110 requires the user to perform a remedial action. In the event that the container 120 has been tampered with, the prescription management system 110 requires a pharmacist to verify that the medication in the container 120 matches the prescription information (e.g., the medication type, pill count, etc.) on the tracking device 130. If the medication in the container 120 does not match the prescription information, the pharmacist may remove the medication and re-fill the prescription. If the medication in the container 120 does match the prescription information, the pharmacist re-verifies the prescription and removes the event associated with the tracking device 130. Once the prescription is re-verified and the prescription management system 110 receives 960 an indication that the appropriate remedial action has been performed, the prescription management system 110 allows 970 the prescription to be released to a customer, and the user completes 980 the sale. A tampering event may be detected at any time (independent of a customer's request to retrieve a filled prescription), and a notification may be sent to a user (e.g., via an on-screen alert or a push notification). In this instance, the user may retrieve the container 120 from the filled prescription holding area and re-verify the prescription, allowing the container 120 to be placed back into the filled prescription holding area.

The prescription management system 110 may detect that a container 120 stores a prescription that was filled at a remote location. When an event is associated with a tracking device 130, the prescription management system 110 requires the user to perform a remedial action. In this instance, the prescription has not yet been verified by a pharmacist and, as a result, the prescription management system 110 does not allow the prescription to be released to a customer. In the event that the container 120 stores a prescription that has not yet been verified, the prescription management system 110 requires a pharmacist to verify that the medication in the container 120 matches the prescription information (e.g., the medication type, pill count, etc.) on the tracking device 130. A pharmacist may verify the prescription manually or through an imaging verification system (e.g., if the pharmacist is operating remotely). If the medication in the container 120 does not match the prescription information, the pharmacist may remove the medication and re-fill the prescription. If the medication in the container 120 does match the prescription information, the pharmacist re-verifies the prescription and removes the event associated with the tracking device 130. Once the prescription is re-verified and the prescription management system 110 receives 960 an indication that the appropriate remedial action has been performed, the prescription management system 110 allows 970 the prescription to be released to a customer, and the user completes 980 the sale. A verification event may be detected at any time (independent of a customer's request to retrieve a filled prescription), and a notification may be sent to a user (e.g., via an on-screen alert or a push notification). In this instance, the user may retrieve the container 120 from the filled prescription holding area and re-verify the prescription, allowing the container 120 to be placed back into the filled prescription holding area.

The prescription management system 110 may detect that a consultation is required before a prescription can be released to the customer. When an event is associated with a tracking device 130, the prescription management system 110 requires the user to perform a remedial action. In this instance, the prescription is associated with a consultation, and, as a result, the prescription management system 110 does not allow the prescription to be released until the consultation is provided to the customer by a pharmacist. Once the consultation is provided to the customer and the prescription management system 110 receives 960 an indication that the appropriate remedial action has been performed, the prescription management system 110 allows 970 the filled prescription to be dispensed from the container 120. Thus, the user completes 980 the sale of the filled prescription to the customer.

While FIG. 9 illustrates that an event may be detected after a user locates and retrieves a container 120, the prescription management system 110 may prevent a user from locating a container 120 if an associated event is detected. Once the appropriate remedial action is performed, then the prescription management system 110 may allow the container 120 to be located by activating the indicator 132 on the associated tracking device 130.

Pharmacy Workflow

In one embodiment, the prescription management system 110 is configured to optimize a pharmacy workflow. Optimizing the pharmacy workflow may include determining an order in which tasks are completed to enable pharmacists and pharmacy technicians to appropriately and efficiently prioritize tasks. Example tasks may include filling prescriptions, verifying prescriptions, providing a consultation to a customer regarding a prescription, responding to events or alerts triggered by the prescription management system 110, checking in containers filled with prescriptions that are received from a remote filling location, other similar tasks within a pharmacy, or some combination thereof. In some embodiments, the prescription management system 110 includes a user interface that displays the tasks to be completed, a priority level associated with each task, a queue indicating an order in which the tasks are to be completed, or some combination thereof.

In one embodiment, a priority level of a task may be defined as "high," "medium," "low," or "none." Each priority level may indicate an amount of time in which the associated task should be completed. For example, a high priority level may indicate that the task is to be completed as soon as possible (e.g., within the next 5 to 10 minutes), a medium priority level may indicate that the task is to be completed within the next few days, a low priority level may indicate that the task is to be completed within the next few weeks, and a no priority level may indicate that the task is to be completed at a user's convenience. In other embodiments, the amount of time associated with each priority level may vary. In some embodiments, the prescription management system 110 may have more or less priority levels. For example, the prescription management system 110 may use a ranking system, ranking each task on a scale of 1 to 5 or on a scale of 1 to 10, or any other suitable scale that provides a desired amount of granularity for the user.

In some embodiments, a workflow learning module (not shown in FIG. 1) of the prescription management system 110 applies machine learning techniques to generate a workflow model that when applied to available tasks to be completed outputs indications of a priority level associated with each task. As part of the generation of the workflow model, the workflow learning module forms one or more training sets of tasks where each training set is associated with a certain priority level by identifying tasks that have been determined to have the certain priority level. In some embodiments, a training set may include several tasks having different priority levels.

The workflow learning module extracts features associated with the tasks of the training set, the features being variables deemed potentially relevant to determining a priority level of the task. Different features may be extracted by the workflow learning module for different tasks. Generally, features may include prescription information (e.g., a type of the medication, a prescription date, a doctor or facility that wrote the prescription, etc.), patient information (e.g., a specific patient associated with the prescription; demographical information of the specific patient such as age, location, residence, medical history; historical prescription pick up data for a specific patient; geographical information; characteristics of patients on a regional level; characteristics of patients on a national level; if the patient is present in the pharmacy; if the patient has notified the pharmacy of a specific pick up time; other patient identifying information; etc.), event or alert information (e.g., a type of event or alert, a risk associated with the event or alert, a date and/or time of the event or alert, etc.), remote filling information (e.g., a specific remote filling facility, a number of prescription orders that were shipped, a date of the shipment, etc.).

An ordered list of the features for a task is herein referred to as the feature vector for the task. In one embodiment, the workflow learning module applies dimensionality reduction (e.g., via linear discriminant analysis (LDA), principle component analysis (PCA), or the like) to reduce the amount of data in the feature vectors for tasks to a smaller, more representative set of data.

The workflow learning module uses supervised machine learning to train the workflow model, with the feature vectors of the training sets serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different embodiments. The workflow model, when applied to the feature vector extracted from a task, outputs an indication of a priority level of the task, such as a rank number or priority type (e.g., high, medium, low, none).

In some embodiments, a validation set is formed of additional tasks, other than those in the training sets, for which the priority level has already been determined. The workflow learning module applies the trained validation workflow model to the tasks of the validation set to quantify the accuracy of the workflow model. Common metrics applied in accuracy measurement include: Precision=TP/(TP+FP) and Recall=TP/(TP+FN), where precision is how many the workflow model correctly predicted (TP or true positives) out of the total it predicted (TP+FP or false positives), and recall is how many the workflow model correctly predicted (TP) out of the total number of tasks that did have a priority level (TP+FN or false negatives). The F score (F-score=2*PR/(P+R)) unifies precision and recall into a single measure. In one embodiment, the workflow learning module iteratively re-trains the workflow model until the occurrence of a stopping condition, such as the accuracy measurement indication that the model is sufficiently accurate, or a number of training rounds having taken place.

After a priority level has been determined for a number of available tasks, the prescription management system 110 may update the user interface for the user based on the priority levels for each tasks. For example, the user interface may display a queue of tasks in the order of the associated priority levels, with high priority level tasks near the top of the queue, and low or no priority level tasks near the bottom of the queue. The user interface may update the order continuously or at specified intervals. For example, as new tasks are made available, the prescription management system 110 may determine a priority level for each task and update the order of tasks displayed in the user interface in real-time. For instance, if a patient is present in the pharmacy or is waiting in the pharmacy drive-thru, the prescription management system 110 may determine that a task for filling the prescription of the patient has a high priority level and may place the task at or near the top of the task queue. As another example, if historical data of a customer indicates (or is predicted based on characteristics of the customer and the order) that the customer typically does not pick up their prescription for several days (e.g., an average between 3-5 days after the prescription date), then the prescription management system 110 may determine that a task for filling the prescription of the patient has a medium priority level and may place the task in the middle of the task queue. As another example, if the prescription management system 110 receives an alert that a temperature sensor on a tracking device 130 or a container 120 has detected a temperature outside of an acceptable range for a medication stored in the container 120, the prescription management system 100 may determine that a task for retrieving the tracking device 130 has a high priority level and may place the task at or near the top of the queue.

While described with relation to a prescription management system, the prescription tracking system and methods described herein are generally applicable to tracking of any product with identifying information. For example, general product tracking and verification may be applied to other more general product tracking, such as a will-call area of a retail store, or any other situation where products are stored with tracking devices.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for managing a filled prescription for a customer, the method comprising:
    storing the filled prescription within a storage container having a tracking device, the tracking device configured to store one or more properties associated with the filled prescription;
    broadcasting a criteria for a property associated with the filled prescription, wherein the criteria comprises a minimum holding period indicating how long a filled prescription has been stored;
    activating an indicator on a tracking device responsive to verifying that a stored property on the tracking device satisfies the broadcasted criteria for the property, wherein satisfying the broadcasted criteria comprises meeting or exceeding the minimum holding period;
    retrieving the tracking device having an activated indicator;
    accessing the storage container attached to the retrieved tracking device to retrieve the filled prescription stored within the storage container;
    converting the retrieved filled prescription to available stock medication.

2. The method of claim 1, wherein the criteria comprises a type of medication, wherein satisfying the broadcasted criteria comprises matching the type of medication.

3. The method of claim 1, further comprising notifying an insurance company associated with the customer to reverse a charge for the filled prescription.

4. The method of claim 1, further comprising printing a label for designating the filled prescription as available stock medication.

5. The method of claim 1, further comprising preventing, in response to a customer request, retrieval of a tracking device determined to store a property that satisfies the broadcasted criteria for the property.

6. The method of claim 5, wherein preventing retrieval comprises blocking a broadcast of a property associated with the customer request.

7. The method of claim 1, wherein a user interface displays a tracking device identifier associated with the tracking device having an activated indicator.

8. The method of claim 7, wherein the user interface displays if the tracking device having an activated indicator has or has not been retrieved.

9. A method for managing a filled prescription for a customer, the method comprising:
   storing the filled prescription within a storage container having a tracking device, the tracking device configured to store one or more properties associated with the filled prescription;
   broadcasting a holding period associated with the filled prescription, the holding period indicating a duration of time that the filled prescription is stored;
   activating an indicator on a tracking device responsive to verifying that a holding period determined based on the stored one or more properties on the tracking device meets or exceeds the broadcasted holding period;
   retrieving the tracking device having an activated indicator;
   accessing the storage container attached to the retrieved tracking device to retrieve the filled prescription stored within the storage container;
   determining if the customer associated with the retrieved filled prescription has authorized filled prescriptions to be delivered to an address of the customer.

10. The method of claim 9, further comprising converting the retrieved filled prescription to available stock medication if the customer has not authorized filled prescriptions to be delivered.

11. The method of claim 9, further comprising marking the retrieved filled prescription for delivery to the customer if the customer has authorized filled prescriptions to be delivered.

* * * * *